US00PP09208P

United States Patent [19]

Mancino

[11] Patent Number: Plant 9,208

[45] Date of Patent: Jul. 18, 1995

[54] BUFFALOGRASS VARIETY CALLED "AZ-143"

[75] Inventor: Charles F. Mancino, Tucson, Ariz.

[73] Assignee: The Arizona Board of Regents on behalf of the University of Arizona, Tucson, Ariz.

[21] Appl. No.: 123,012

[22] Filed: Sep. 17, 1993

[51] Int. Cl.[6] ..... A01H 5/00
[52] U.S. Cl. ..... Plt./90
[58] Field of Search ..... Plt. 90

[56] References Cited

U.S. PATENT DOCUMENTS

P.P. 7,539 5/1991 Engelke et al. ..... Plt./90
P.P. 8,475 11/1993 Riordan et al. ..... Plt./90

OTHER PUBLICATIONS

National Buffalo Grass Test—1991, Progress Report 1992, National Turfgrass Evaluation Program, United States Department of Agriculture, and National Turfgrass Federation, Inc. (1992).

Marcum, K. B. and M. C. Engelke, "Rooting Characteristics of Buffalograsses Included in the National Turfgrass Evaluation Program Trail", PR-4979, Texas Turfgrass Research—1992. The Texas Agricultural Experiment Station, College Station, Tex. (1982).

Rickard, Jack, "In search of a better grass: UA lab sowing seeds for the future", *Tucson Golf* 4–6 (1993).

*Primary Examiner*—James R. Feyrer
*Attorney, Agent, or Firm*—Quarles & Brady

[57] ABSTRACT

A new and distinct variety of turf-type Buffalograss called AZ-143 is characterized by its shorter plant height, shorter leaf length, and superior rooting characteristics when compared with commercially avaiable turf-type Buffalograsses. AZ-143 has been shown to perform well in a wide range of environmental conditions.

3 Drawing Sheets

FIELD OF THE INVENTION

The present invention relates to a new and distinct variety of herbaceous ornamental Buffalograss, characterized by its shorter plant height, shorter leaf length, and superior rooting characteristics than commercially avaiable turf-type Buffalograsses. The claimed variety also exhibits better overall color, density, ground cover, and pest resistance than many turf-type Buffalograsses.

BACKGROUND OF THE INVENTION

Buffalograss is a native North American short-prairie grass adapted to warm, semiarid and subhumid, unirrigated conditions. It is well adapted to the Great Plains states and is one of the most important grazing grasses of the region. Buffalograss is found naturally from western Minnesota to central Montana, south to northwestern Iowa, Texas, western Louisiana, Arizona, and northern Mexico. While buffalograss has long been used for range and low-maintenance turf, its utility for such purposes waned as the use of irrigation increased.

However, as new water-conservation measures have been sought, a resurgent need has arisen for lower quality, utility turfs for roadsides, airfields, lawns and other minimum maintenance areas. As such, significant effort has been expended in breeding and selection to improve the appearance of buffalograss. As a result, the physical characteristics of buffalograsses used for turf has improved. These characteristics include better green color, better sod-forming ability, higher density, shorter plant height, and finer leaf texture. As the appearance of buffalograsses has improved, they are increasingly being used in areas where aesthetic turf is desirerd but where low maintenance is also desired. Such areas include golf course fairways and roughs, home lawns and commercial properties.

SUMMARY OF THE INVENTION

AZ-143 is distinguished from existing varieties of buffalograss in that it is a vegetatively reproduced female plant having 2n chromosomes=60. AZ-143 has a shorter plant height than other known buffalograsses. AZ-143 is also distinguished on the basis of its high percentage of living ground cover in spring and summer. AZ-143 also has distinctive leaf hairiness and DNA fingerprint profiles when compared to other market varieties.

AZ-143 was a single clonal plant vegetatively propagated from a Tucson, Ariz. lawn that contained both buffalograss and bermudagrass.

BRIEF DESCRIPTION OF THE DRAWINGS

FIG 2 shows the distinguishing leaf hairiness of the claimed variety.

DESCRIPTION OF THE CLAIMED VARIETY

Figure 1:
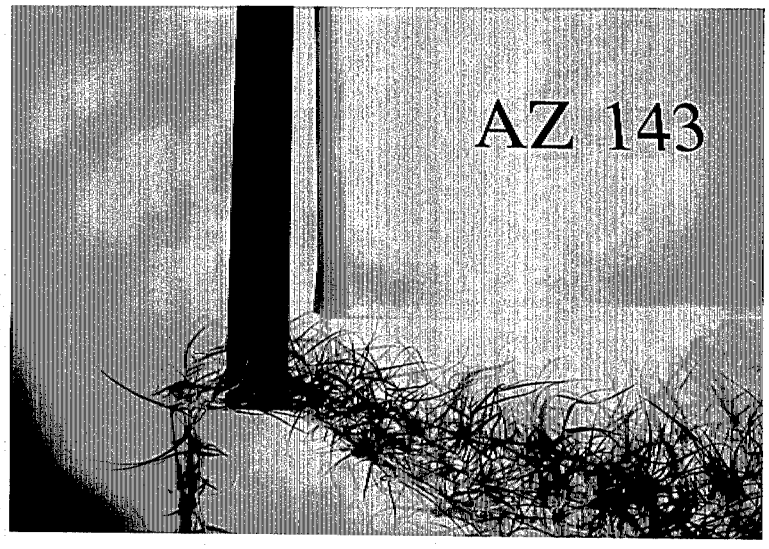
FIG. 1 depicts the buffalograss variety AZ-143.

The AZ-143 variety claimed herein, and showin in FIG. 1 meets each of the above requirements and offers aesthetics comparable or better than other commercially avaiable Buffalograsses. Reference is now made to Table 1 which compares AZ-143 to four commercially available buffalograsses (NE-315, NE-609, Prairie, and Texoka) in greenhouse tests. These tests have shown AZ-143 to have a shorter plant height than each of the four other tested cultivars. The leaf length of AZ-143 is shoter than Prairie, NE-609, and Texoka, and is roughly comparable to that of NE-315. AZ-143 is intermediate in leaf width, being similar to Prairie, NE-609, and NE-315. The leaf width is significantly narrower than that of Texoka.

AZ-143 is equivalent to Prairie, NE-609, NE-315, and Texoka for primary and secondary stolon number. The primary stolon length of AZ-143 is comparable to that of Prairie and NE-609 and superior to that of NE-315 and Texoka. The internode width of AZ-143 is slightly narrower than that of Prairie or NE-609.

The new AZ-143 variety and twenty-one other Buffalograsses were compared in a comprehensive national United States Department of Agriculture (USDA) evaluation of overall month-to-month growth quality, leaf texture, density, coverage, frost and drought tolerance, seasonal color, disease and pest resistance, vertical growth and seasonal seedhead rating at twenty-two test sites. According to these criteria, AZ-143 was the third highest quality Buffalograsses overall, after NE-315 and NE-378, having superior ability to perform well as a turfgrass over a very wide range of environmental conditions, including growth at sites outside its normal zone of adaptation. AZ-143 was also distinguished in that its percentage of living ground cover in spring and summer was highest on average among the cultivars tested at eleven sites. For instance, at Santa Clara, Calif., 99% of the AZ-143 in the test plot was alive. At Norton, Va., 75% and 65% living ground cover was observed in spring and summer, respectively, which was more than twice as great as the next closest cultivars, including NE-315. In addition, the overall summer density of AZ-143 was very high, being just slightly less dense than NE-315.

In a leaf spot test conducted in Beltsville, Md., AZ-143 was highly resistant to leafspots caused by Bipolaris spp. AZ-143 was somewhat less resistant than NE-609 or Prairie, but was more than twice as resistant as NE-315. Similarly, AZ-143 is more resistant to eriophyid mite damage than NE-315 and is comparable to NE-609.

TABLE 1

| Variety | Stolon number 1° | Stolon number 2° | Plant height (mm) | Leaf length (mm) | Leaf width (mm) |
|---|---|---|---|---|---|
| Prairie | 1.8a | 4.1a | 150ab | 104b | 1.6c |
| NE-609 | 1.8a | 1.7a | 163a | 105b | 1.9ab |
| AZ-143 | 1.7a | 3.2a | 79c | 81c | 1.7bc |
| NE-315 | 2.0a | 2.0a | 108bc | 78c | 1.9ab |
| Texoka | 2.5a | 3.2a | 170a | 133a | 2.0a |

| Variety | Internode length (mm) 3rd | Internode length (mm) 4th | Internode width (mm) 3rd | Internode width (mm) 4th | Primary Stolon length (mm) |
|---|---|---|---|---|---|
| Prairie | 47b | 49b | 1.5a | 1.4a | 370a |
| NE-609 | 57a | 63a | 1.2ab | 1.3ab | 366a |
| AZ-143 | 48b | 49b | 1.0b | 1.1ab | 362a |
| NE-315 | 29d | 31c | 0.9b | 0.9b | 246b |
| Texoka | 37c | 38c | 0.9b | 0.9b | 272b |

AZ-143 has also been shown to have superior rooting characteristics when compared in a separate study to the twenty-one other Buffalograsses in the National Turfgrass Evaluation program. AZ-143 had the greatest number of roots in the lower root sections and had the highest total root mass and root mass per 10 cm root section of the tested buffalograsses. AZ-143 was also shown to develop roots at the 60 cm depth before most other Buffalograsses, after about the same growth time as NTDG-1, NTDG-4, and NTDG-5.

AZ-143 is also characterized by its high shoot growth. Root and shoot growth were monitored in a laboratory test setting.

Classification:

*Botanic.*—Buchloe dactyloides (Nutt) Engelm.

Chromosome number: 2n chromosomes=60 (hexapolid).

Form: Monocot gramineae.

Growth habit: The variety grows as a perennial female plant, with a stoloniferous growth habit that allows it to be propagated vegetatively. The variety is able to spread under non-competitive conditions when conditions are favorable for stolon production. It has excellent sod strength allowing it to be efficiently harvested and installed as sod. It has a fibrous root system which can achieve depth of over 1 meter under appropriate soil conditions. It will produce a dense, short, fine-textured turf with good color throughout most of the growth season.

Establishment rate:

*Plugs.*—Eight to twelve weeks with irrigation.

*Sod.*—One to two weeks.

*Springs.*—Not recommended.

Adaptation: Canadian border to central Mexico, with optimum growth seen in the central great plains. The variety is very well adapted to the arid southwestern United States. Although it will grow in temperate and humid climates, it is not recommended for these environments.

Blade:

*Shape.*—Long and slender.

*Length.*—About 5 cm to 13 cm, typical 8 cm.

*Width.*—About 1 mm to 2.5 mm, typical 1.7 mm.

Figure 2:
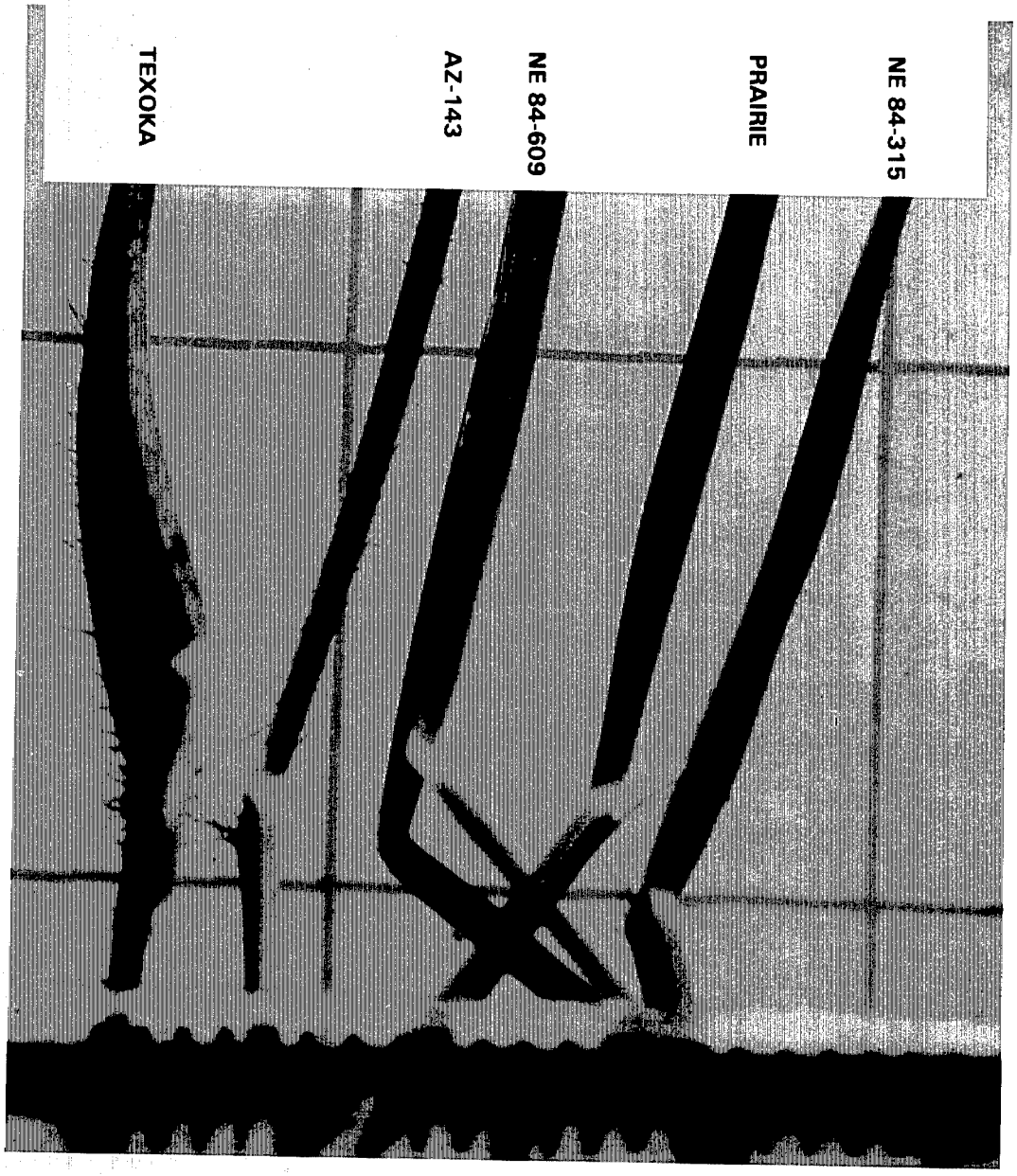
FIG. 2 depicts in detail the leaf structure of AZ-143 and other buffalograss varieties.

*Hairs.*—Both abaxial and adaxial hairs, as is shown in FIG. 2.

Mature plant height: About 3.1 cm to about 12.4 cm with fertilization, about 7.9 cm typical.

Primary internode: Length for the third internode from the tip ranges from about 3 cm to about 13 cm, about 4.8 cm typical. For the fourth internode from the tip, a typical internode length is 4.9 cm, with a range from about 3.9 cm to 6.0 cm. The primary internode diameter for the third internode from the tip is 1 mm. For the fourth internode from the tip, the primary internode diameter is typically 1.1 mm, with a ranger from about 1 mm to 1.5 mm.

Node pigmentation: predominantly green, though sometimes purple along your stolons.

Stolon color: Non-dormant is typically green, the upper surface having the color designation 177B, the lower surface 139C. The dormant stolon color is typically brown (164C).

Leaf color: The non-dormant leaf color is light green (138B). The dormant leaf color is brown (164C). The color designations noted above were assigned according to the R.H.S. Colour Chart, first published in 1966 by The Royal Horticultural Society, London, England.

Soils: Loamy clay to sandy loam soils with slightly acid to alkaline pH.

Female inflorescence: 0 to 6 per square foot, typically 2. The flower parts do not differ from those of other members of the species significantly in size, shape, color or timing.

Figure 3:
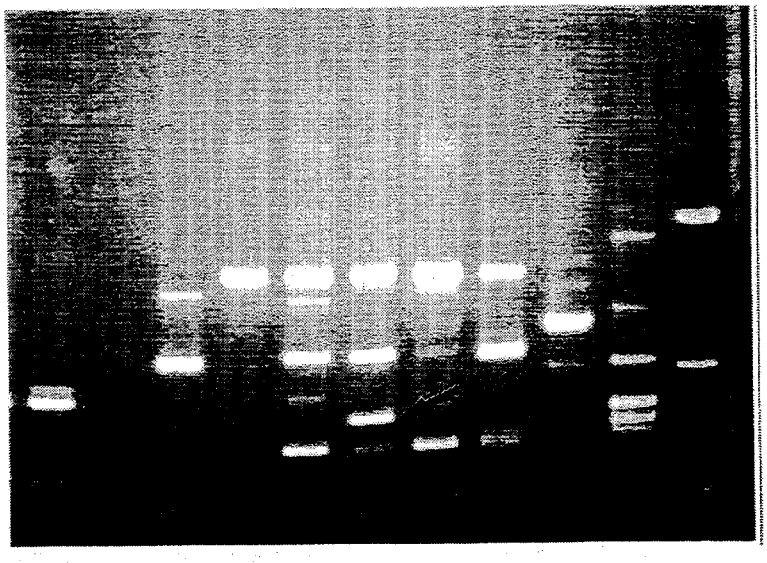
FIG. 3 depicts the PCR DNA polymorphism analysis for several buffalograsses including AZ-143, a bermudagrass, and a saltgrass. The polymorphism analysis of AZ-143 shows a characteristic fragment of AZ-143 that migrates between molecular size markers 1198 and 678.

FIG. 3 depicts the PCR DNA polymorphism fingerprint for buffalograsses NE84-609, NE84-315, AZ-143, Prairie, and Texoka, and Tifway bermudagrass and an ecotype of Distichlis spp. (saltgrass). The fingerprint was obtained using the polymerase chain reaction to amplify polymorphic DNA markers using random primers. The arrow indicates a unique band observed in AZ-143 but not in the other tested buffalograsses. The band migrates between molecular size markers 1198 and 678.

AZ-143 Buffalograss is a vegetatively propagated female plant. The above-noted characteristics of this variety breed true to form in suceeding vegetatively propagated generations. The parentage of AZ-143 is unknown, although the plant from which AZ-143 was derived was obtained from an established Tucson, Ariz. lawn that dated back at least thirty years. The established lawn contained both Buffalograss and Bermudagrass (*Cynodon dactylion*). Over the years, the lawn had been flood irrigated and mowed periodically. The exact nature of the original Buffalograss in the lawn is not known. The Buffalograss probably originated in Oklahoma or Texas as a common Buffalograss brought to Arizona by the USDA Soil Conservation Service.

The new variety was isolated from the established Tuscon lawn as follows. Twenty-four turf plugs (5 cm diameter) was removed, replicated in field plots, and allowed to reach full ground cover. At one and two years after field plot replication, mower and drought stress were imposed on these plots. A superior female plant labeled AZ-143 was then selected on the basis of its persistance and appearance. The selected plant was vegetatively propagated at the University of Arizona, Tucson, Ariz. from cuttings.

I claim:

1. A new and distinct variety of Buffalograss substantially as shown and described.

* * * * *